United States Patent
Sanematsu et al.

(10) Patent No.: US 9,392,680 B2
(45) Date of Patent: Jul. 12, 2016

(54) PLASMA GENERATOR, AND CLEANING AND PURIFYING DEVICE APPARATUS AND SMALL-SIZED ELECTRICAL APPLIANCE USING PLASMA GENERATOR

(75) Inventors: Wataru Sanematsu, Kyoto (JP); Akihiko Saitoh, Osaka (JP); Kenji Narita, Osaka (JP); Masaharu Machi, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 317 days.

(21) Appl. No.: 13/980,263

(22) PCT Filed: Jan. 25, 2012

(86) PCT No.: PCT/JP2012/051516
§ 371 (c)(1),
(2), (4) Date: Jul. 17, 2013

(87) PCT Pub. No.: WO2012/108260
PCT Pub. Date: Aug. 16, 2012

(65) Prior Publication Data
US 2013/0291794 A1    Nov. 7, 2013

(30) Foreign Application Priority Data
Feb. 8, 2011  (JP) .................................. 2011-024933

(51) Int. Cl.
*H05H 1/46* (2006.01)
*H05H 1/24* (2006.01)
(Continued)

(52) U.S. Cl.
CPC ................. *H05H 1/24* (2013.01); *A45D 27/46* (2013.01); *A61L 2/14* (2013.01); *B08B 7/0035* (2013.01);
(Continued)

(58) Field of Classification Search
CPC .... H05H 1/24; H05H 2001/4682; H05H 1/46

USPC .......................... 315/111.51, 111.21, 111.71; 156/345.48; 204/192.1, 298.08
See application file for complete search history.

(56) References Cited

U.S. PATENT DOCUMENTS

| | | | |
|---|---|---|---|
| 2005/0189278 A1 | 9/2005 | Iijima et al. | |
| 2011/0133651 A1* | 6/2011 | Chistyakov | H01J 37/32009 315/111.41 |
| 2011/0259851 A1* | 10/2011 | Brouk et al. | 216/61 |

FOREIGN PATENT DOCUMENTS

| | | | | |
|---|---|---|---|---|
| GB | 1292933 A | * | 2/1970 | .............. B01F 3/04 |
| GB | 1292933 A | | 10/1972 | |

(Continued)

OTHER PUBLICATIONS

Title:JP2008178870A (Plasma Generator, Method for producing radical, and washing and clearning apparatus), Author: Uda Keiichiro, Date:Aug. 7, 2008, (Translation).*

(Continued)

*Primary Examiner* — Thai Pham
*Assistant Examiner* — Wei Chan
(74) *Attorney, Agent, or Firm* — McDermott Will & Emery LLP

(57) ABSTRACT

A plasma generator 1 includes a first electrode 12 provided in a gas storage section 5; and a second electrode 13 separated from the first electrode 12 and provided in a manner such that at least the portion coupled with the first electrode 12 is in contact with a liquid 17 in a liquid storage section 4. Electric discharge is caused between the first electrode 12 and the second electrode 13 so as to produce plasma in a gas region in the liquid 17 in the liquid storage section and produce hydroxyl radical from water contained in the liquid 17 and oxygen contained in the gas. A voltage controller 60 controls a voltage applied by a plasma power source 15 depending on conditions.

6 Claims, 8 Drawing Sheets

(51) Int. Cl.
  *B08B 7/00* (2006.01)
  *A61L 2/14* (2006.01)
  *C01B 13/11* (2006.01)
  *A45D 27/46* (2006.01)
  *C02F 1/78* (2006.01)

(52) U.S. Cl.
  CPC .............. *C01B 13/11* (2013.01); *H05H 1/2406* (2013.01); *C01B 2201/64* (2013.01); *C01B 2201/90* (2013.01); *C02F 1/78* (2013.01); *H05H 2001/2412* (2013.01)

(56) References Cited

FOREIGN PATENT DOCUMENTS

| | | | |
|---|---|---|---|
| JP | 03-072995 | A | 3/1991 |
| JP | 05-295485 | B2 | 3/1991 |
| JP | 2004-202454 | A | 7/2004 |
| JP | 2004-268003 | A | 9/2004 |
| JP | 2006-253056 | A | 9/2006 |
| JP | 2007-207540 | A | 8/2007 |
| JP | 4111858 | B | 4/2008 |
| JP | 2008-178870 | A | 8/2008 |
| JP | 2008178870 | A * | 8/2008 |
| JP | 2010-177002 | A | 8/2010 |

OTHER PUBLICATIONS

Title:JP2008178870A (Plasma Generator, Method for producing radical, and washing and clearning apparatus), Author: Uda Keiichiro, Date:Aug. 7, 2008, (Translation of the drawings).*
Title: JP2008178870A (Plasma Generator, Method for producing radical, and washing and clearning apparatus), Author: Uda Keichiro, Date:Aug. 7, 2008 (Translation).*
Title: JP2008178870A (Plasma Generator, Method for producing radical, and washing and clearning apparatus), Author: Uda Keichiro, Date:Aug. 7, 2008 (Translation of Drawings).*
Tittle: GB1292933 A (Method and Apparatus for Purifying a Natural Body of Water), Date: Feb. 23, 1970, Author: Harold Vincent Anthony George Perry Fulton.*
Chinese Search Report issued in Chinese Application No. 201280006503.9, dated Feb. 2, 2015, with English translation.
International Search Report issued in International Application No. PCT/JP2012/051516 with Date of mailing Mar. 6, 2012.
Chinese Search Report issued in Chinese Application No. 201280006503.9 on Oct. 10, 2015, with English Translation.
Chen, J. et al., "Research progress on generation mechanism and determination of hydroxyl radical in electrochemical system", Journal of Zhejiang University of Technology, vol. 36, No. 4, Aug. 2008. (With English Abstract).

* cited by examiner

PLASMA GENERATOR, AND CLEANING AND PURIFYING DEVICE APPARATUS AND SMALL-SIZED ELECTRICAL APPLIANCE USING PLASMA GENERATOR

RELATED APPLICATIONS

This application is the U.S. National Phase under 35 U.S.C. §371 of International Application No. PCT/JP2012/051516, filed on Jan. 25, 2012, which in turn claims the benefit of Japanese Application No. 2011-024933, filed on Feb. 8, 2011, the disclosures of which Applications are incorporated by reference herein.

TECHNICAL FIELD

The present invention relates to a plasma generator, and a cleaning and purifying apparatus and a small-sized electrical appliance each using the plasma generator.

BACKGROUND ART

There are known apparatuses to produce a radical and the like in gas bubbles contained in a liquid by causing electric discharge in the liquid so as to reform the liquid (for example, refer to Patent Document 1).

CITATION LIST

Patent Literature

Patent Document 1: Japanese Patent No. 4111858

SUMMARY OF INVENTION

However, a large amount of radicals may not be produced efficiently even if a predetermined voltage is applied between electrodes, since the state of liquid to be treated is not constant.

It is an object of the present invention to obtain a plasma generator capable of efficiently producing a large amount of radicals, and a cleaning and purifying apparatus and a small-sized electrical appliance each using the plasma generator.

A plasma generator according to a first aspect of the present invention includes: a liquid storage section that stores a liquid containing water; a gas storage section that stores a gas; a partition provided with a gas passage to introduce the gas in the gas storage section into the liquid storage section, and separating the liquid storage section from the gas storage section; a first electrode provided in the gas storage section; a second electrode separated from the first electrode and provided in a manner such that at least a portion coupled with the first electrode is in contact with the liquid in the liquid storage section; a gas supply unit that supplies a gas containing oxygen to the gas storage section so that the gas in the gas storage section is delivered under pressure into the liquid storage section via the gas passage; a plasma power source that applies a predetermined voltage between the first electrode and the second electrode to cause electric discharge between the first electrode and the second electrode, and thereby convert the gas introduced into the gas storage section into plasma; and a voltage controller that controls the voltage applied by the plasma power source depending on a condition of the liquid in the liquid storage section.

A plasma generator according to a second aspect of the present invention includes a sensing member that senses an impedance of the liquid in the liquid storage section at a fixed time interval, wherein the voltage controller controls the plasma power source to apply a higher voltage as the impedance of the liquid sensed by the sensing member is higher, and controls the plasma power source to apply a lower voltage as the impedance of the liquid sensed by the sensing member is lower.

A plasma generator according to a third aspect of the present invention includes a sensing member that senses a temperature of the liquid in the liquid storage section at a fixed time interval, wherein the voltage controller controls the plasma power source to apply a higher voltage as the temperature of the liquid sensed by the sensing member is higher, and controls the plasma power source to apply a lower voltage as the temperature of the liquid sensed by the sensing member is lower.

A plasma generator according to a fourth aspect of the present invention includes a sensing member that senses a pH of the liquid in the liquid storage section at a fixed time interval, wherein the voltage controller controls the plasma power source to apply a lower voltage as the pH of the liquid sensed by the sensing member is higher, and controls the plasma power source to apply a higher voltage as the pH of the liquid sensed by the sensing member is lower.

A plasma generator according to a fifth aspect of the present invention includes a sensing member that senses a presence or absence of gas bubbles in the liquid in the liquid storage section at a fixed time interval, wherein the voltage controller controls the plasma power source to apply a voltage only when the gas bubbles are sensed in the liquid in the liquid storage section.

A cleaning and purifying apparatus according to a sixth aspect of the present invention includes the plasma generator according to any one of the above aspects.

A small-sized appliance according to a seventh aspect of the present invention includes the plasma generator according to any one of the above aspects or the cleaning and purifying apparatus according to the above aspect.

DESCRIPTION OF EMBODIMENTS

Hereinafter, embodiments according to the present invention will be explained in detail with reference to the drawings.

(First Embodiment)

A plasma generator 1 according to the present embodiment includes a case member 2 formed in a substantially cylindrical shape. Note that the case member is not limited to the cylindrical shape, and it may be formed in a prism.

Figure 1:
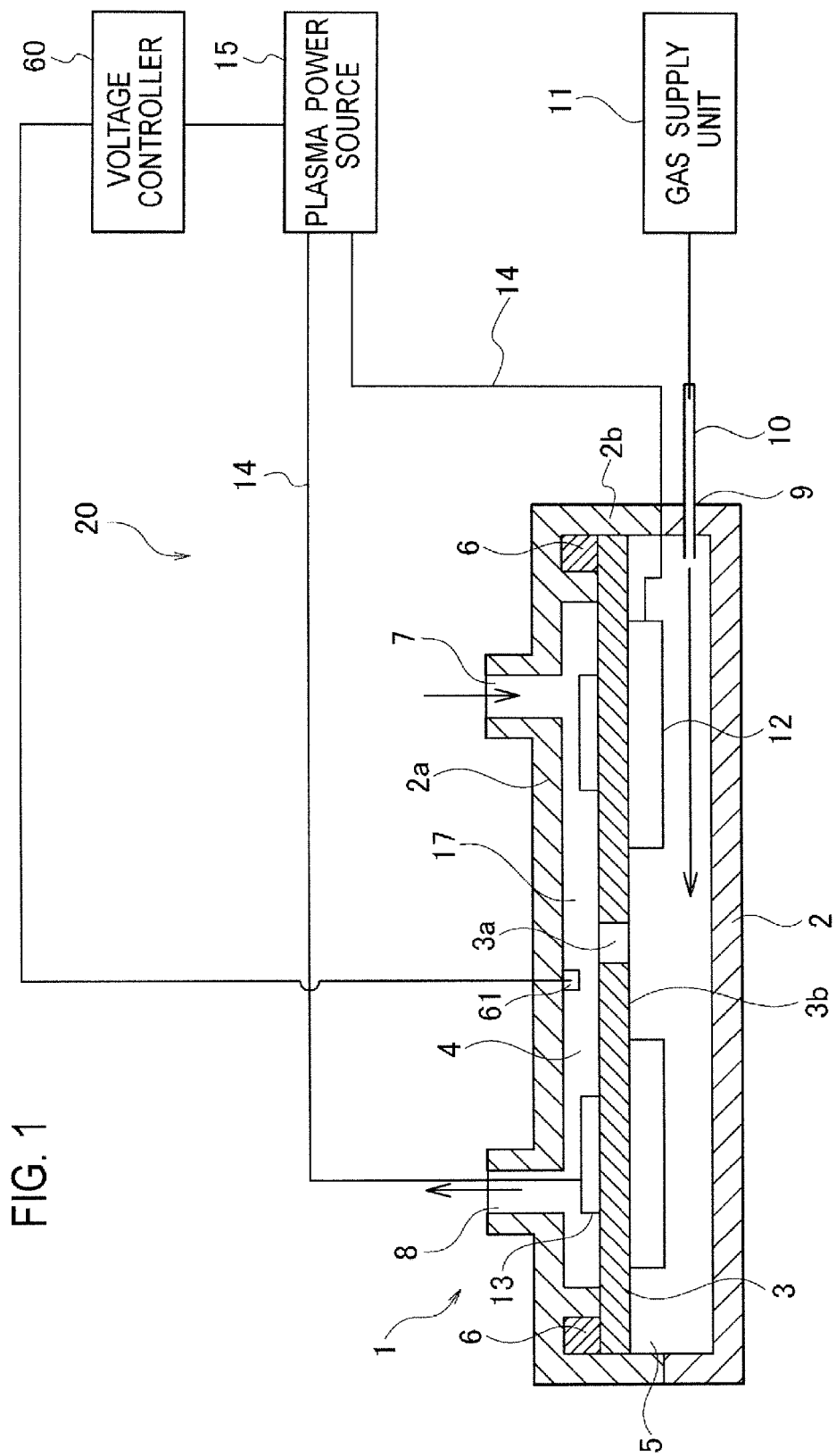
FIG. 1 is a schematic partial cross-sectional view showing a configuration of a plasma generator according to an embodiment of the present invention.

As shown in FIG. 1, a ceramic member 3 is provided inside of the case member 2 to divide the case member 2 into an upper area and a lower area.

In the present embodiment, the upper area in the inner space of the case member 2 divided by the ceramic member 3 serves as a liquid storage section 4 to store a liquid 17 containing water, and the lower area serves as a gas storage section 5 to store a gas.

As described above, the ceramic member 3 according to the present embodiment serves as a partition to separate the liquid storage section 4 from the gas storage section 5.

A ring-shaped sealing member 6 is attached along the periphery of the liquid storage section 4 to seal the gap between the case member 2 and the ceramic member 3, so as to prevent the liquid 17 in the liquid storage section 4 from leaking from the gap between the case member 2 and the ceramic member 3 into the gas storage section 5.

A liquid inlet 7 is provided on the upper wall (the wall on the liquid storage section 4 side) 2a of the case member 2 to introduce the liquid 17 into the liquid storage section 4, and a liquid outlet 8 is provided on the upper wall 2a to discharge the liquid 17 introduced into the liquid storage section 4 to the outside.

A gas inlet 9 is provided at the bottom of the side wall 2b of the case member 2 so that the gas storage section 5 communicates with the outside. A pipe (a gas introduction passage) 10 is inserted into the gas inlet 9. The gas storage section 5 is connected to a gas supply unit 11 via the pipe 10. In the present embodiment, a gas containing at least oxygen (O2) is supplied to the gas storage section 5 from the gas supply unit 11.

The ceramic member 3 is provided with a gas passage 3a through which the gas introduced into the gas storage section 5 from the gas supply unit 11 is delivered to the liquid storage section 4.

The gas supply unit 11 according to the present embodiment thus functions to supply the gas containing at least oxygen to the gas storage section 5 in a manner such that the gas in the gas storage section 5 is delivered under pressure to the liquid storage section 4 via the gas passage 3a.

In the present embodiment, the diameter of the hole in the gas passage 3a is set approximately in the range from 1 μm to 10 μm so as to prevent the liquid 17 stored in the liquid storage section 4 from leaking from the gas passage 3a into the gas storage section 5.

The plasma generator 1 includes a first electrode 12 provided in the gas storage section 5, and a second electrode 13 separated from the first electrode 12 and provided in such a manner that at least the portion coupled with the first electrode 12 is in contact with the liquid 17 in the liquid storage section 4.

In particular, the substantially doughnut-shaped first electrode 12 and the substantially doughnut-shaped second electrode 13 are provided in the gas storage section 5 and in the liquid storage section 4, respectively.

As shown in FIG. 1, the substantially doughnut-shaped first electrode 12 is positioned on the surface 3b of the ceramic member 3 in the gas storage section 5 in a manner such that the center thereof serves as the gas passage 3a. The surface of the first electrode 12 is covered with a dielectric material (not shown in the figure).

The second electrode 13 is provided in the liquid storage section 4 in such a manner that at least the portion coupled with the first electrode 12 is in contact with the liquid 17 in the liquid storage section 4. The second electrode 13 is also positioned in a manner such that the center thereof serves as the gas passage 3a. Namely, the first electrode 12 and the second electrode 13 are arranged in a concentric pattern.

In the plasma generator according to the present embodiment, the doughnut-shaped first electrode 12 is provided in the gas storage section 5 so as to be prevented from coming into contact with the liquid 17 introduced into the liquid storage section 4.

The second electrode 13 is provided in the liquid storage section 4 in such a manner that the second electrode 13 (at least the portion coupled with the first electrode 12) is in contact with the liquid 17 introduced into the liquid storage section 4.

Figure 2:
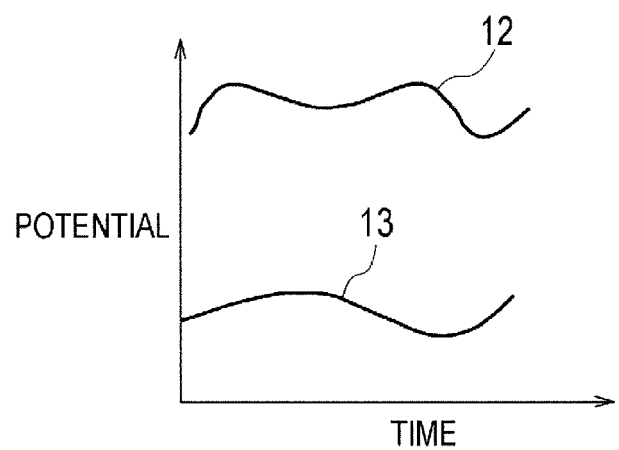
FIG. 2 is a view showing a relationship between a potential on a first electrode and a potential on a second electrode of a plasma generator according to an embodiment of the present invention.

The first electrode 12 and the second electrode 13 are each electrically connected to a plasma power source 15 via leads 14 (refer to FIG. 1), so that a predetermined voltage is applied between the first electrode 12 and the second electrode 13. Here, as shown in FIG. 2, the potential on the second electrode 13 in the liquid 17 is set to be lower than the potential on the first electrode 12 in the gas, so as to prevent the risk of electrical shock.

Next, the performance of the plasma generator 1 and the method for producing hydroxyl radical are explained below.

First, a gas containing oxygen is supplied to the gas storage section 5 in a manner such that the gas in the gas storage section 5 is delivered under pressure to the liquid storage section 4 via the gas passage 3a (a step of supplying a gas).

In the present embodiment, as shown in FIG. 1, the gas containing oxygen based on air (the flow rate is approximately in the range from 0.01 L/min to 1.0 L/min (in the range from 10 cc/min to 1000 cc/min)) is delivered to the gas storage section 5 from the gas supply unit 11 via the pipe 10. In this case, the pressure to deliver the gas is set approximately in the range from 0.0098 MPa to 0.49 MPa (in the range from 0.1 kgf/cm2 to 5 kgf/cm2).

As described above, the gas supply unit 11 functions to supply the gas (air) in the atmosphere. Here, the flow rate of the gas supplied is controlled by a flow rate controller provided in the gas supply unit 11. Alternatively, the gas supply unit 11 may function to supply several types of gases (for example, gases having different oxygen concentrations) in addition to the gas in the atmosphere, and may be provided with a gas-type regulator to selectively supply one of or some of the several types of gases.

When the gas is supplied to the gas storage section 5, the pressure in the gas storage section 5 is changed approximately to the range from 0.11 MPa to 0.59 MPa (from 1.1 kgf/cm2 to 6 kgf/cm2) due to the increased pressure (in addition to the atmospheric pressure), so that the gas storage section 5 is in a state of positive pressure. The positive pressure in the gas storage section 5 causes a flow of the gas toward the liquid storage section 4 from the gas storage section 5 through the gas passage 3a. The positive pressure in the gas storage section 5 also contributes to preventing the liquid 17 stored in the liquid storage section 4 from leaking into the gas storage section 5 through the gas passage 3a.

Figure 3:
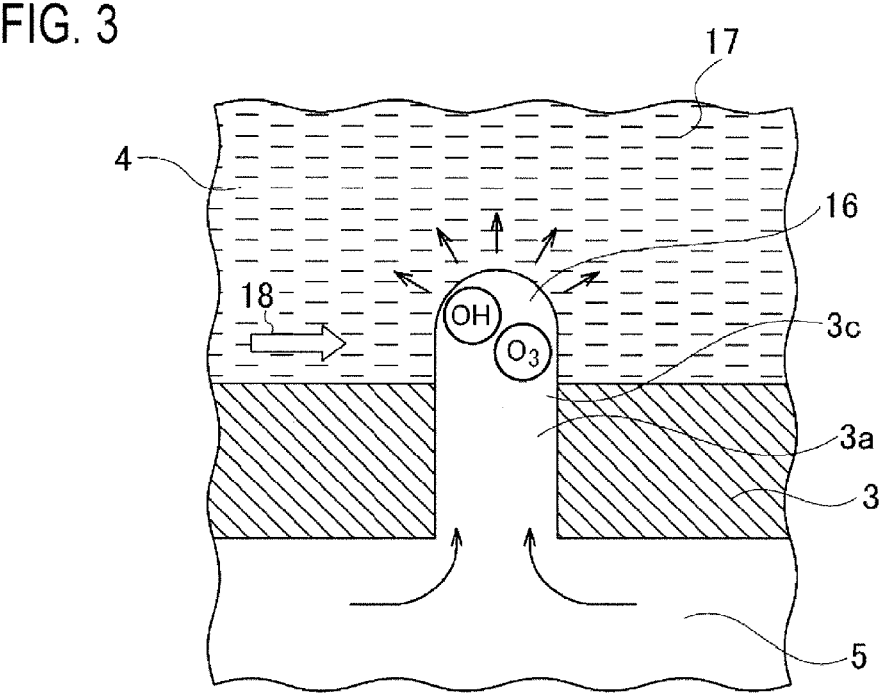
FIG. 3 is a partially enlarged cross-sectional view schematically showing a particular situation to explain the performance of a plasma generator according to an embodiment of the present invention.

As shown in FIG. 3, when the gas containing oxygen is supplied to the gas storage section 5 as described above, fine gas bubbles 16 containing oxygen are developed at the opening end 3c of the gas passage 3a on the liquid storage section 4 side (the upper side in FIG. 1) (a step of developing gas bubbles).

Then, a predetermined voltage is applied between the first electrode 12 and the second electrode 13 by the plasma power source 15. The applied voltage is preferably capable of glow discharge under atmospheric pressure (power: approximately from 10 W to 100 W).

Here, the conditions of the liquid 17, such as the impedance of the liquid 17, the temperature of the liquid 17, the pH of the liquid 17 and the presence or absence of gas bubbles in the liquid 17, vary with time. According to the present embodiment, the voltage applied by the plasma power source 15 is controlled depending on the conditions of the liquid 17.

For example, a sensing member 61 senses the impedance of the liquid 17 in the liquid storage section 4 at a fixed time interval, and notifies a voltage controller 60 of the obtained results. The voltage controller 60 thus controls the plasma power source 15 to apply a higher voltage as the impedance of the liquid 17 sensed by the sensing member 61 is higher. The voltage controller 60 controls, on the other hand, the plasma power source 15 to apply a lower voltage as the impedance of the liquid 17 sensed by the sensing member 16 is lower. The level of the impedance is determined by comparing with the preceding impedance. Accordingly, the voltage can be controlled in proportion to the impedance of the liquid 17 by providing the feedback of the information of the sensed impedance to the voltage controller 60.

Alternatively, the sensing member 61 may sense the temperature of the liquid 17 in the liquid storage section 4 at a fixed time interval, and notifies the voltage controller 60 of the obtained results. In this case, the voltage controller 60 controls the plasma power source 15 to apply a higher voltage as the temperature of the liquid 17 sensed by the sensing member 61 is higher. The voltage controller 60 controls, on the other hand, the plasma power source 15 to apply a lower voltage as the temperature of the liquid 17 sensed by the sensing member 16 is lower. The level of the temperature is determined by comparing with the preceding temperature. Accordingly, the voltage can be controlled in proportion to the sensed temperature of the liquid 17 by providing the feedback of the information of the sensed temperature to the voltage controller 60.

Alternatively, the sensing member 61 may sense the pH of the liquid 17 in the liquid storage section 4 at a fixed time interval, and notifies the voltage controller 60 of the obtained results. In this case, the voltage controller 60 controls the plasma power source 15 to apply a lower voltage as the pH of the liquid 17 sensed by the sensing member 61 is higher. The voltage controller 60 controls, on the other hand, the plasma power source 15 to apply a higher voltage as the pH of the liquid 17 sensed by the sensing member 16 is lower. The level of the pH is determined by comparing with the preceding pH. Accordingly, the voltage can be controlled in inverse proportion to the pH of the liquid 17 by providing the feedback of the information of the sensed pH to the voltage controller 60.

Alternatively, the sensing member 61 may sense the presence or absence of gas bubbles in the liquid 17 in the liquid storage section 4 at a fixed time interval, and notifies the voltage controller 60 of the obtained results. In this case, the voltage controller 60 controls the plasma power source 15 to apply a voltage only when the gas bubbles are sensed in the liquid 17 in the liquid storage section 4. The presence or absence of the gas bubbles is determined based on a predetermined reference value. Accordingly, the ON-OFF state of the voltage can be controlled depending on the presence or absence of the gas bubbles in the liquid 17 by providing the feedback of the information of the sensed condition to the voltage controller 60.

Once the predetermined voltage is applied between the first electrode 12 and the second electrode 13, electric discharge is caused between the first electrode 12 and the second electrode 13 in a gas atmosphere under atmospheric pressure or higher. Here, a method for producing plasma under atmospheric pressure has been reported in, for example, Document A (Sachiko Okazaki, "Atmospheric Pressure Glow Discharge Plasma and Its Applications", Review Speech: 20th JSPF Annual Meeting).

The electric discharge produces plasma in the gas region in the liquid 17 in the liquid storage section 4, so as to produce ozone and hydroxyl radical from water contained in the liquid or oxygen contained in the gas (a step of producing hydroxyl radical).

According to the present embodiment, a potential difference is caused in the gas inside the gas bubbles 16 (the gas present around the gas-liquid boundary in the liquid 17 in the liquid storage section 4) so as to produce the plasma. The potential difference caused around the gas-liquid boundary (adjacent to the opening end 3c of the gas passage 3a facing the liquid 17) where the hydroxyl radical is easily produced, can produce a larger amount of ozone and hydroxyl radical. Note that, in the present embodiment, the ozone and hydroxyl radical can be produced also in the gas bubbles 16 delivered into the liquid storage section 4 in addition to the gas bubbles 16 present adjacent to the opening end 3c of the gas passage 3a facing the liquid 17.

The ozone and hydroxyl radical thus produced are delivered to the liquid storage section 4 in association with the gas flow described above.

According to the present embodiment, the gas bubbles 16 containing the hydroxyl radical and the like are separated from the ceramic member (the partition) 3 and then released into the liquid 17 by the flow of the liquid 17 in the liquid storage section 4 (a step of releasing gas bubbles).

Figure 4:
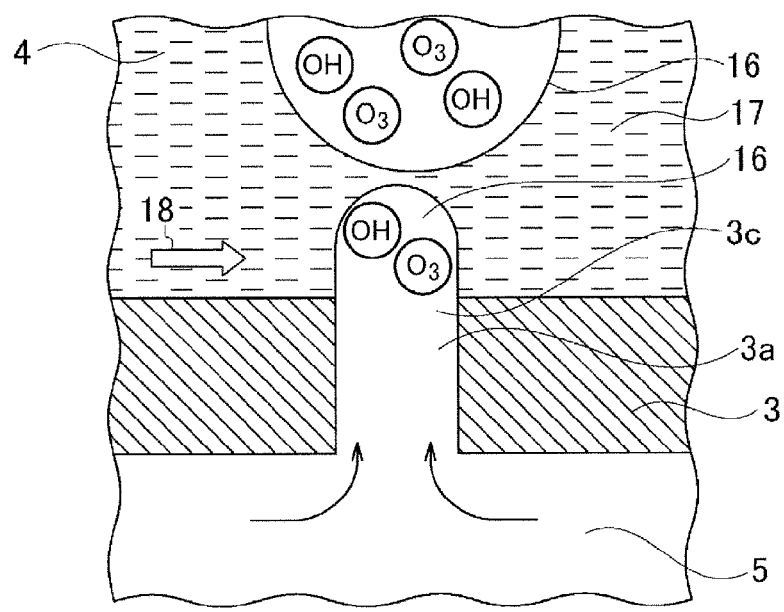
FIG. 4 is a partially enlarged cross-sectional view schematically showing a situation following the situation shown in FIG. 3.

In particular, the liquid 17 is introduced to the liquid storage section 4 where the gas bubbles 16 are developed, so as to generate the flow of the liquid 17 (refer to arrow 18 in FIG. 3 and FIG. 4). As shown in FIG. 4, when the liquid 17 flowing in the direction of the arrow 18 hits the gas bubbles 16 being developed, the gas bubbles 16 are subjected to a separation force caused by the flow of the liquid 17 and are thereby released into the liquid 17 from the opening end 3c.

Since the gas bubbles 16 released into the liquid 17 are fine gas bubbles, the released gas bubbles 16 are dispersed in the liquid 17 in all directions without being emitted immediately into the atmosphere. A number of the dispersed fine gas bubbles 16 are easily dissolved in the liquid 17. At this point, the ozone contained in the gas bubbles 16 is dissolved into the liquid 17 and as a result, the ozone concentration in the liquid 17 is immediately increased.

Here, Document B (Masayoshi Takahashi, "Improvement in Aquatic Environment by Microbubbles and Nanobubbles"; Aquanet, 2004. 6) has reported that the fine gas bubbles 16 containing the ozone and several types of radicals generally tend to be negatively-charged. Therefore, a number of the gas bubbles 16 easily adhere to materials such as organic substances, oil and fat substances, dyes, proteins and bacteria (not shown in the figures) contained in the liquid 17. The organic substances and the like in the liquid 17 are resolved by the ozone or several types of radicals dissolved in the liquid 17, or by the ozone or several types of radicals contained in the gas bubbles 16 adhering to the organic substances and the like.

For example, the hydroxyl radical has relatively high energy that is approximately 120 kcal/mol. Such energy is greater than bond energy (up to 100 kcal/mol) of a double bond between nitrogen atoms (N=N), a double bond between carbon atoms (C=C), or a double bond between a nitrogen atom and a carbon atom (N=C). Therefore, the organic substances produced by the bond of nitrogen and/or carbon are resolved since the bond in the organic substances is easily broken by the hydroxyl radical. Here, the ozone and hydroxyl radical contributing to such a resolution of the organic substances are environmentally-friendly substances since the ozone and hydroxyl radical are not persistent (unlike chlorine and the like) but disappear with time.

As described above, the plasma generator 1 according to the present embodiment includes the voltage controller 60 that controls the voltage applied by the plasma power source 15 according to the conditions of the liquid 17 in the liquid storage section 4. As a result, the electric discharge can be stably caused regardless of the varied conditions of the liquid 17 and therefore, a large amount of the OH radical can be produced efficiently because the amount of the OH radical produced per amount of power increases.

In particular, the voltage controller 60 controls the plasma power source 15 to apply a higher voltage as the impedance of the liquid 17 is higher, and controls the plasma power source 15 to apply a lower voltage as the impedance of the liquid is lower. Accordingly, a large amount of the OH radical can be produced efficiently in parallel with the varied impedance of the liquid 17.

Alternatively, the voltage controller 60 controls the plasma power source 15 to apply a higher voltage as the temperature of the liquid 17 is higher, and controls the plasma power source 15 to apply a lower voltage as the temperature of the liquid is lower. Accordingly, a large amount of the OH radical can be produced efficiently in parallel with the varied temperature of the liquid 17.

Alternatively, the voltage controller 60 controls the plasma power source 15 to apply a lower voltage as the pH of the liquid 17 is higher, and controls the plasma power source 15 to apply a higher voltage as the pH of the liquid is lower. Accordingly, a large amount of the OH radical can be produced efficiently in association with the varied pH of the liquid 17.

Alternatively, the voltage controller 60 controls the plasma power source 15 to apply a voltage only when gas bubbles are present in the liquid 17 in the liquid storage section 4. Accordingly, the ON-OFF state of the voltage can be controlled depending on the presence or absence of the gas bubbles in the liquid.

According to the present embodiment, the first electrode 12 is provided in the gas storage section 5, and the second electrode 13 is provided in such a manner that at least the portion coupled with the first electrode 12 is in contact with the liquid in the liquid storage section 4. The plasma is produced in the gas region inside the liquid 17 in the liquid storage section 4 by causing the electric discharge between the first electrode 12 and the second electrode 13, so that the hydroxyl radical is produced from water contained in the liquid 17 and oxygen contained in the gas. According to the configuration and method described above, the electric discharge can be caused between the first electrode 12 and the second electrode 13 without being influenced largely by the electrical resistance of the liquid 17 and therefore, the gas can be converted into plasma more reliably. Accordingly, a large amount of ozone and radical can be produced more stably.

According to the present embodiment, the liquid 17 is introduced into the liquid storage section 4, and the first electrode 12 for producing plasma is provided in the gas storage section 5 that is defined by the ceramic member 3. Therefore, the first electrode 12 does not come into contact with the liquid 17 and is not influenced by the electrical resistance of the liquid 17. As a result, the electric discharge can be stably caused between the first electrode 12 and the second electrode 13. Further, the ozone and hydroxyl radical can be stably produced from water and oxygen since the gas containing oxygen introduced into the gas storage section 5 is surely converted into plasma.

According to the present embodiment, the gas containing oxygen is introduced into the gas storage section 5, so that the gas storage section 5 is in the state of positive pressure, and the flow of the gas from the gas storage section 5 toward the liquid storage section 4 through the gas passage 3a is generated. The ozone and hydroxyl radical are produced inside the gas bubbles 16 developed at the opening end 3c of the gas passage 3a facing the liquid 17 in association with the gas flow. The gas bubbles 16 having grown to a predetermine size are separated from the opening end 3c by the flow of the liquid 17 and dispersed in the liquid 17.

Namely, in the present embodiment, the ozone and hydroxyl radical are produced in the gas which forms the gas bubbles 16 (the gas present around the gas-liquid boundary in the liquid 17 in the liquid storage section 4). The gas containing the ozone and hydroxyl radical is dispersed as the fine gas bubbles 16 in the liquid 17 in all directions. Accordingly, the ozone and several types of radicals can be delivered into the liquid 17 efficiently in quite a short period of time after the production but before the disappearance of the ozone and several types of radicals.

Since the fine gas bubbles 16 containing the ozone and several types of radicals are dispersed in the liquid 17 in all directions, the ozone concentration in the liquid 17 is increased, and the gas bubbles 16 adhere to the organic substances contained in the liquid 17. As a result, the organic substances or bacteria can be effectively resolved by the ozone dissolved in the liquid 17 and the several types of radicals contained in the gas bubbles 16 adhering to the organic substances.

Further, since the first electrode 12 and the second electrode 13 that produce the plasma are formed into a doughnut shape, the entire size of the plasma generator 1 excluding the plasma power source 15 and the gas supply unit 11 can be reduced. Accordingly, the plasma generator 1 can be easily installed in existing apparatuses. In addition, a space occupied by the plasma generator 1 can be minimized when installing in new apparatuses.

When the gas supply unit 11 includes the gas-type regulator to regulate the type of the gas, the amount of the ozone and hydroxyl radical produced can be adjusted.

In this case, if the gas supply unit 11 functions to supply air in the atmosphere, the gas can be supplied more easily.

Further, if the flow rate controller controls the flow rate of the supplied gas, the plasma can be produced more stably.

(Second Embodiment)

Next, an example of a cleaning and purifying apparatus using the plasma generator 1 will be explained below.

Figure 5:
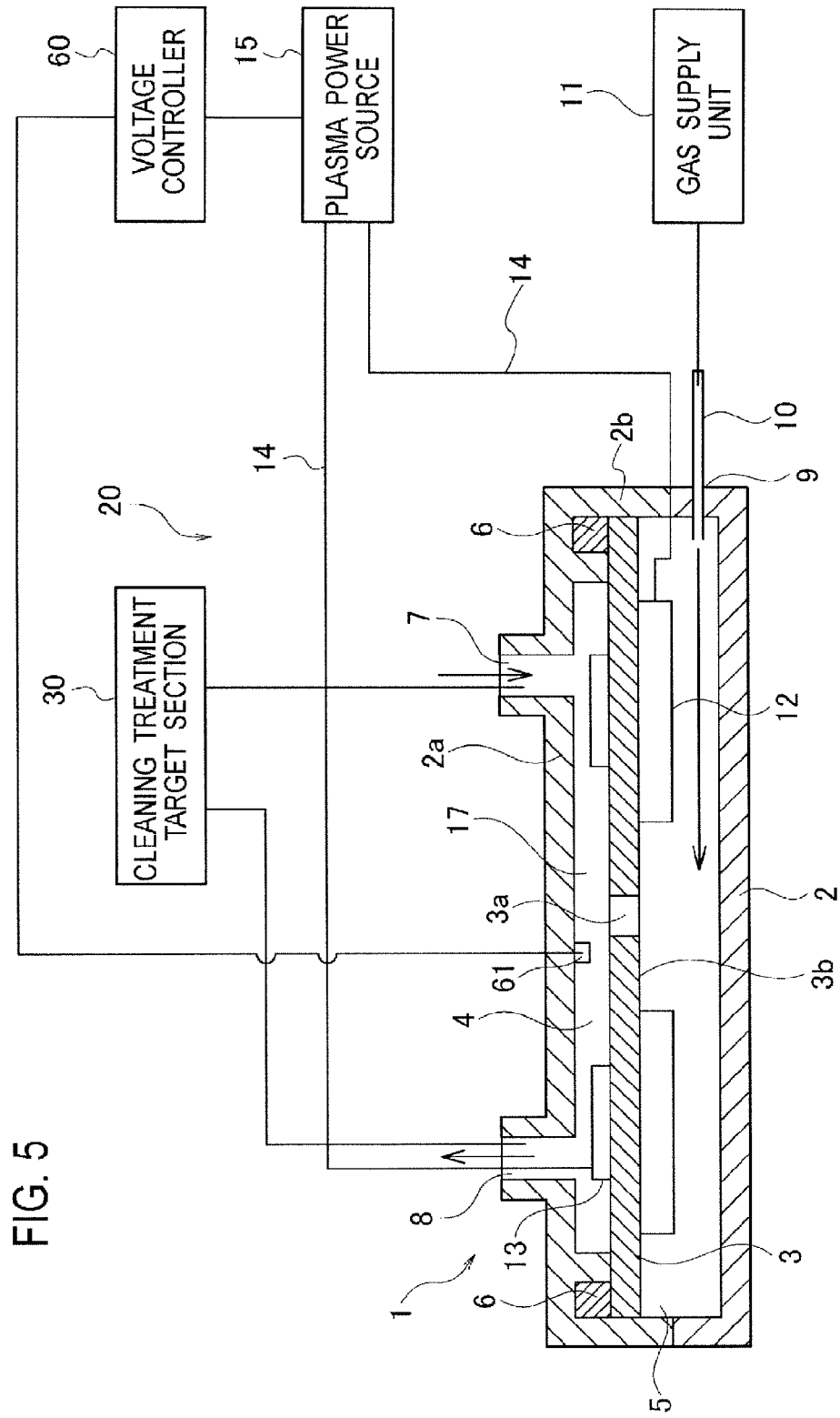
FIG. 5 is a schematic partial cross-sectional view showing a configuration of a cleaning and purifying apparatus according to an embodiment of the present invention.

As shown in FIG. 5, a cleaning and purifying apparatus 20 includes the above-described plasma generator 1. In the cleaning and purifying apparatus 20 according to the present embodiment, a pipe (a liquid introduction passage) 21 to introduce the treated liquid 17 from a cleaning treatment target section 30 into the liquid storage section 4, is connected to the liquid inlet 7 of the case member 2 that houses the ceramic member 3. In addition, a pipe (a liquid discharge passage) 22 to deliver the liquid inside the liquid storage section 4 to the cleaning treatment target section 30, is connected to the liquid outlet 8.

The following is an explanation of the performance of the cleaning and purifying apparatus 20.

As shown in FIG. 5, a gas containing oxygen based on air and having a predetermined flow rate is delivered from the gas supply unit 11 to the gas storage section 5 via the pipe (the gas introduction passage) 10. Once the gas storage section 5 is shifted to the positive pressure state, the gas starts to flow from the gas storage section 5 toward the liquid storage section 4 through the gas passage 3a.

At this point, the treated liquid 17 is introduced from the cleaning treatment target section 30 into the liquid storage section 4 through the pipe (the liquid introduction passage) 21 and the liquid inlet 7.

Then, a predetermined voltage is applied between the first electrode 12 and the second electrode 13 so that electric discharge is caused between the first electrode 12 and the second electrode 13. This electric discharge produces plasma in the gas region in the liquid 17 in the liquid storage section 4, and produces ozone and hydroxyl radical from water contained in the liquid 17 and oxygen contained in the gas (refer to FIG. 3).

The produced ozone and several types of radicals are delivered to the liquid storage section 4 along with the gas flow. At this point, the gas bubbles being developed are separated by the flow of the liquid 17, and released into the liquid as the fine gas bubbles 16.

The fine gas bubbles 16 released into the liquid are dispersed in all directions. A number of the dispersed fine gas bubbles 16 are easily dissolved in the liquid 17 together with the ozone and hydroxyl radical contained in the gas bubbles 16, and the ozone concentration is thus increased. In addition, a number of the gas bubbles 16 containing the ozone and hydroxyl radical easily adhere to the organic substance contained in the liquid 17. Further, fine organic substances adhere to a number of the gas bubbles 16.

The ozone or radical dissolved in the liquid 17, or the ozone or radical contained in the gas bubbles 16 adhering to the organic substances, thus effectively resolves the organic substances in the liquid 17. The liquid 17 cleaned in a manner such that the organic substances are resolved, returns to the cleaning treatment target section 30 from the liquid outlet 8 through the pipe (the liquid discharge passage) 22 so as to be reused.

The cleaning and purifying apparatus 20 described above was exemplified by a usage mode (usage mode A) in which the liquid 17 is cleaned and purified inside the case member 2. Alternatively, another usage mode (usage mode B) in which the liquid 17 containing the fine gas bubbles dispersed therein is supplied to a predetermined device as a cleaning liquid, may also be applicable to the present embodiment.

In the latter case, the cleaning and purifying apparatus 20 operates as follows.

First, the fine gas bubbles 16 containing the ozone and hydroxyl radical are dispersed in the liquid 17 introduced into the case member 2, and the ozone and hydroxyl radical contained in the fine gas bubbles 16 are thus dissolved in the liquid 17. At this point, fine organic substances adhere to a number of the gas bubbles 16.

Then, the liquid 17 is supplied as a cleaning liquid to the cleaning treatment target section 30. In the cleaning treatment target section 30, the organic substances are effectively resolved by the ozone or radical dissolved in the liquid 17, or by the ozone or radical contained in the gas bubbles 16 adhering to the organic substances.

In the case of using the cleaning and purifying apparatus in usage mode A, the cleaning and purifying apparatus may be used for purification of various types of liquids such as warm water stored in bathtubs, rainwater, foul water and sewage water. In the case of usage mode B, the liquid 17 is water acting as a purifying liquid used for, for example, various types of appliances such as a washing machine and a dishwasher, health appliances such as a mouthwashing device, and sanitary appliances such as a lavatory basin. In addition to these appliances, a wide variety of industrial applications such as washing of food and cleaning of industrial products in manufacturing processes may be possible.

In the present embodiment, since the cleaning and purifying apparatus 20 includes the plasma generator 1, the cleaning and purifying apparatus 20 can produce a large amount of radicals efficiently.

When the cleaning and purifying apparatus 20 is provided with a position adjuster that adjusts the position of the plasma generator 1, the plasma can be stabilized more reliably.

(Third Embodiment)

An example of a small-sized appliance using the plasma generator 1 will be explained below with reference to FIG. 6 to FIG. 8. The following is an explanation of a cleaning and purifying apparatus to clean a head unit of an electric shaver as a hair removing device.

Figure 6:
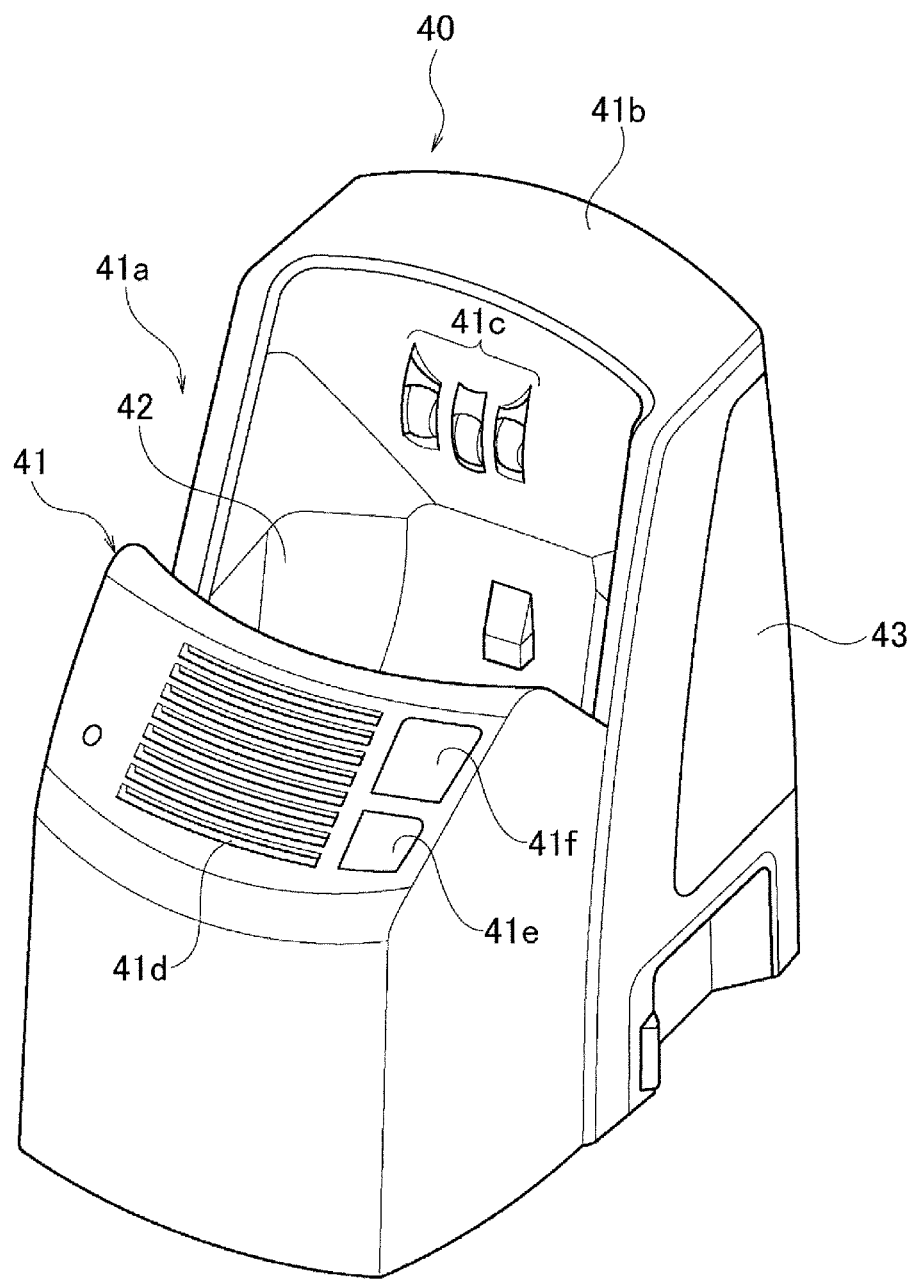
FIG. 6 is a perspective view showing a specific example of a small-sized appliance including a plasma generator according to an embodiment of the present invention.
Figure 7:
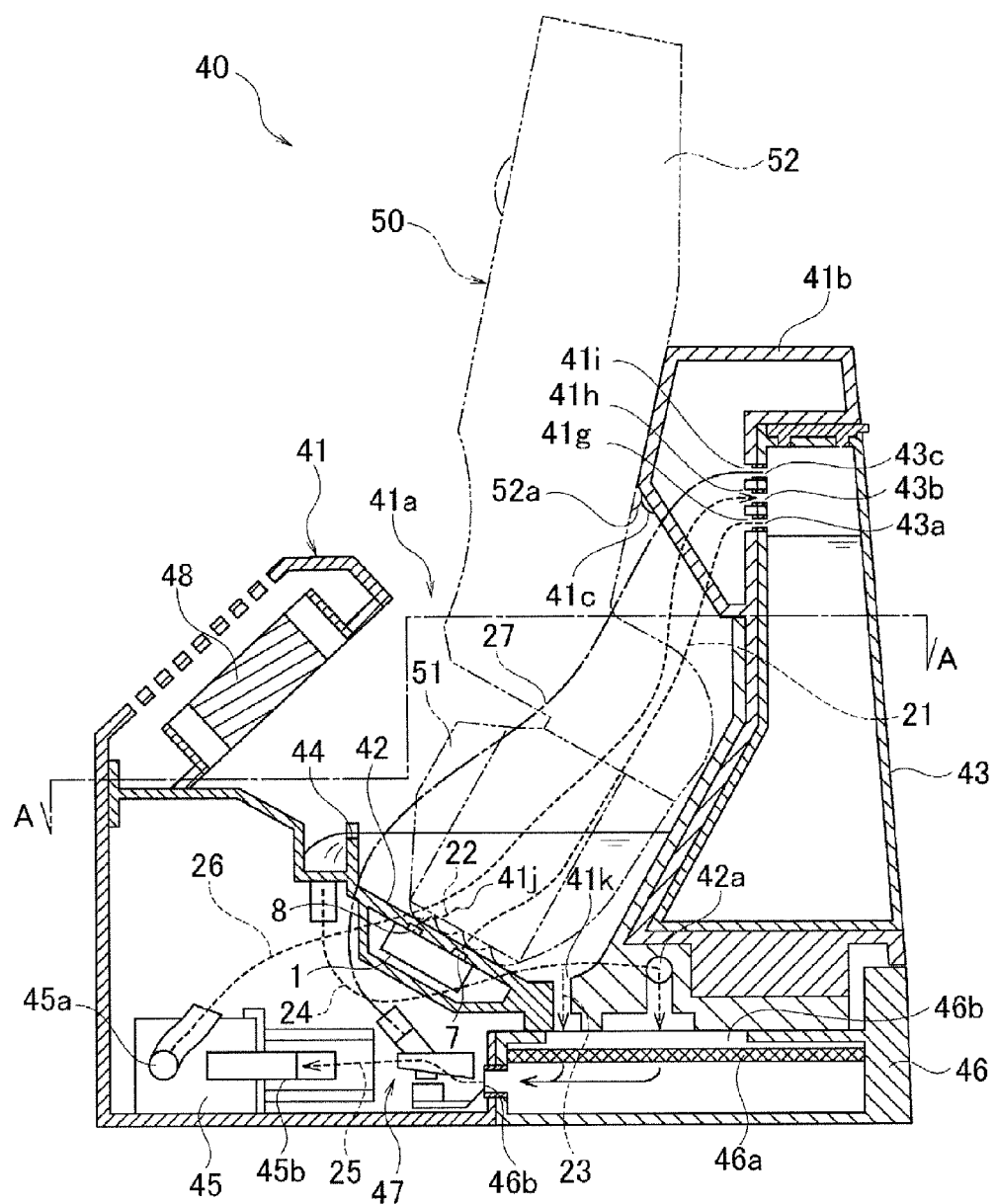
FIG. 7 is a side cross-sectional view of the small-sized appliance shown in FIG. 6.
Figure 8:
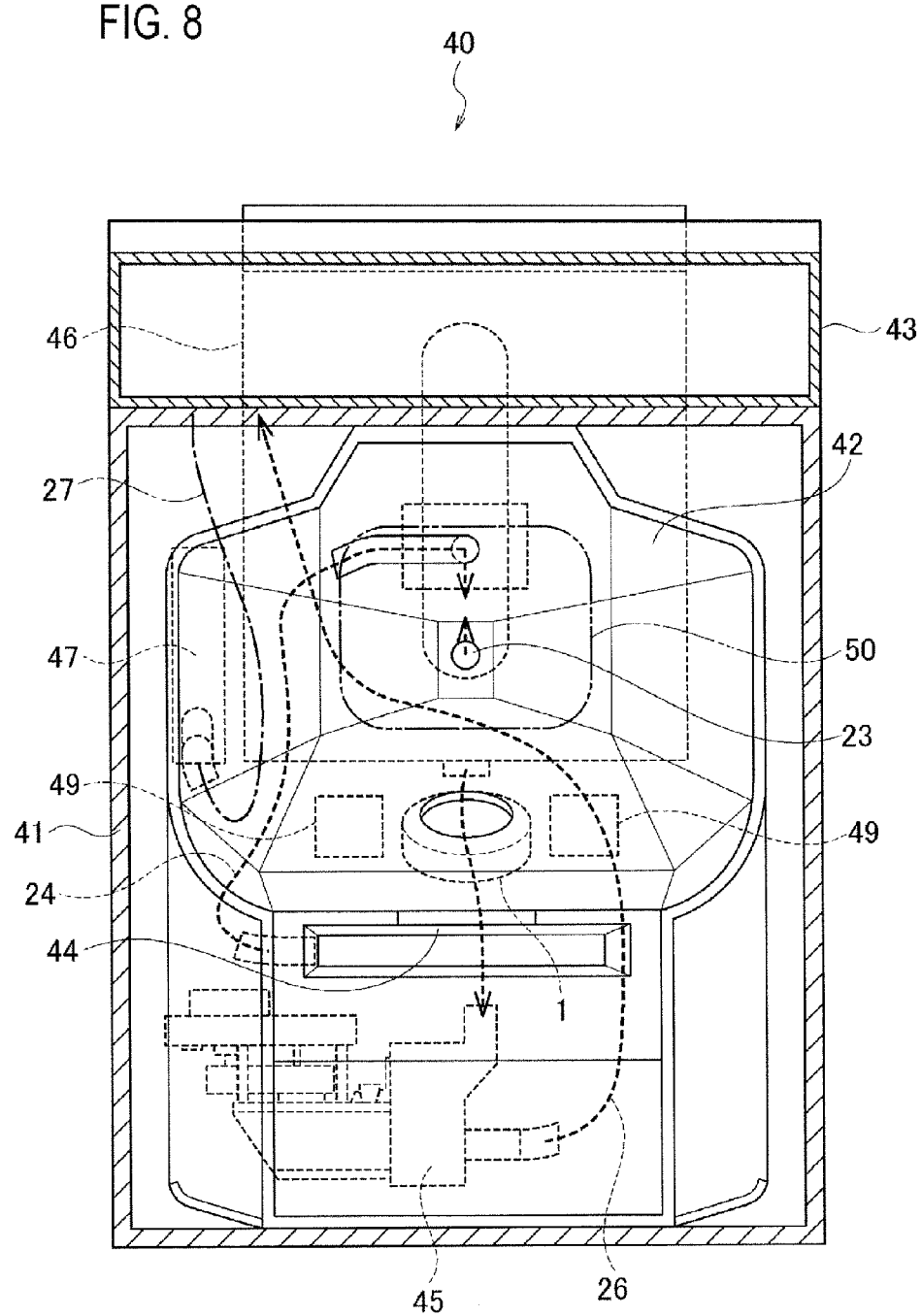
FIG. 8 is a cross-sectional view taken along the line A-A in FIG. 7.

A cleaning and purifying apparatus 40 as a small-sized appliance shown in FIG. 6 to FIG. 8 cleans a head unit 51 of an electric shaver 50 serving as a hair removing device. Namely, the cleaning and purifying apparatus 40 is used in usage mode B. The head unit 51 of the electric shaver 50 corresponds to the cleaning treatment target section 30.

As shown in FIG. 6 to FIG. 8, the cleaning and purifying apparatus 40 includes a case 41 having the opening 41a through which the electric shaver 50 with the head unit 51 directed downward is inserted, and a receiving plate 42 that receives the head unit 51 inserted through the opening 41a.

The cleaning and purifying apparatus 40 further includes a tank 43 that stores a liquid, an overflow section 44 that communicates with the receiving plate 42, and a pump 45 that cyclically supplies the liquid stored in the tank 43 to the liquid inlet 7. In addition, the cleaning and purifying apparatus 40 includes a cartridge 46 having a filter 46a for filtration of the liquid, an opening-closing valve 47 that controls the airtight state inside the tank 43, and a circulation path in which the liquid is circulated.

The circulation path includes the pipe (the liquid introduction passage) 21 to introduce the liquid stored in the tank 43 into the liquid inlet 7, the pipe (the liquid discharge passage) 22 to deliver the liquid discharged from the liquid outlet 8 into the receiving plate 42, a path 23 (a discharge passage) to introduce the liquid discharged from the receiving plate 42 into the cartridge 46, a path 24 to introduce the liquid discharged from the overflow section 44 into the cartridge 46, a path 25 to introduce the liquid discharged from the cartridge 46 into the pump 45, and a path 26 to introduce the liquid delivered from the pump 45 into the tank 43. The opening-closing valve 47 is connected to the tank 43 via an airtight path 27. Next, the respective components are explained in detail below.

The case 41 includes a stand 41b coming into contact with the grip 52 of the electric shaver 50 on the back side, and holds the electric shaver 50 inserted from the opening 41a with the receiving plate 42. As shown in FIG. 6, the stand 41b is provided, on the front surface, with contact members 41c that detect the insertion of the electric shaver 50 in the cleaning and purifying apparatus 40 when a terminal 52a provided on the back surface of the grip 52 comes into contact with the contact members 41c. In addition to this detecting function, the electric shaver 50 has a function to output several control signals and driving power.

The case 41 houses a fan 48 in the front and upper portion to dry the head unit 51 after finishing cleaning. The case 41 is provided, on the front side, with a ventilation window 41d for the fan 48, an operation button 41e to start the cleaning operation, and a lamp 41f to indicate the operating state. The case 41 is provided with the tank 43 on the back side having connecting ports 41g, 41h and 41i each communicating with ports 43a, 43b and 43c, respectively. The connecting port 41g is connected to the pipe (the liquid introduction passage) 21, the connecting port 41h is connected to the path 26, and the connecting port 41i is connected to the airtight path 27.

The receiving plate 42 is a recess formed in a manner such that the head unit 51 fits therein, and is provided with the plasma generator 1 on the back side of the bottom wall. The cleaning and purifying apparatus 40 may be provided with a position adjuster that adjusts the position of the plasma generator 1. For example, the receiving plate 42 may be provided, on the back side of the bottom wall, with an arm member to which the plasma generator 1 is swingably fixed so that the position adjuster can adjust and place the plasma generator 1 in a horizontal position. This contributes to constantly keeping the plasma generator 1 in the horizontal position and thereby producing the plasma more stably.

The plasma generator 1 includes the liquid inlet 7 connected to the pipe (the liquid introduction passage) 21, and the liquid outlet 8 connected to the pipe (a liquid discharge passage) 22. The bottom wall of the receiving plate 42 is provided with a supply port 41j connected to the pipe (the liquid discharge passage) 22 and a discharge port 41k connected to the path 23.

The receiving plate 42 is provided with heaters 49 on the back side of the bottom wall (refer to FIG. 8). The heaters 49 dry the head unit 51 in association with the fan 48.

The overflow section 44 is provided on the front side of the receiving plate 42. The receiving plate 42 and the overflow section 44 are integrally formed in the present embodiment. The inlet of the overflow section 44 is connected to the receiving plate 42, and the outlet of the overflow section 44 is connected to the path 24. The path 24 connects the outlet of the overflow section 44 to the cartridge 46 via a junction port 42a provided on the rear side of the receiving plate 42.

The tank 43 is provided, on the front surface, with the outflow port 43a, the inflow port 43b, and the ventilation port 43c to release the tank 43 from the airtight condition. The ventilation port 43c opens and closes to control liquid discharge from the outflow port 43a. The tank 43 is detachably provided on the back side of the case 41. When the tank 43 is attached to the case 41, the outflow port 43a is connected to the connecting port 41g via the pipe (the liquid introduction passage) 21 so as to communicate with the liquid inlet 7 of the plasma generator 1. The inflow port 43b is connected to the connecting port 41h via the path 26 so as to communicate with the delivery port 45a of the pump 45. The ventilation port 43c is connected to the connecting port 41i via the airtight path 27 so as to communicate with the opening-closing valve 47.

The cartridge 46 is formed into a substantially box shape that houses the filter 46a therein, and has an inflow port 46b on the upper side and an outflow port 46c on the front side. The cartridge 46 is detachably provided on the bottom and rear side of the case 41. When the cartridge 46 is attached to the case 41, the inflow port 46b is connected to the discharge port 41k via the path 23 (the discharge passage), and connected to the outlet of the overflow section 44 via the path 24. The outflow port 46c is connected to a suction port 45b of the pump 45 via the path 25.

Accordingly, the cleaning liquid produced in a manner such that the fine gas bubbles 16 containing the ozone and hydroxyl radical are dispersed into the liquid introduced into the plasma generator 1 from the tank 43, is supplied to the receiving plate 42 from the connecting port 41j. Namely, the produced cleaning liquid is supplied to the head unit 51 serving as the cleaning treatment target section 30. Accordingly, the ozone or radical dissolved in the liquid (the cleaning liquid), or the ozone or radical contained in the gas bubbles 16 can effectively resolve the organic substances adhering to the head unit 51.

Figure 9:
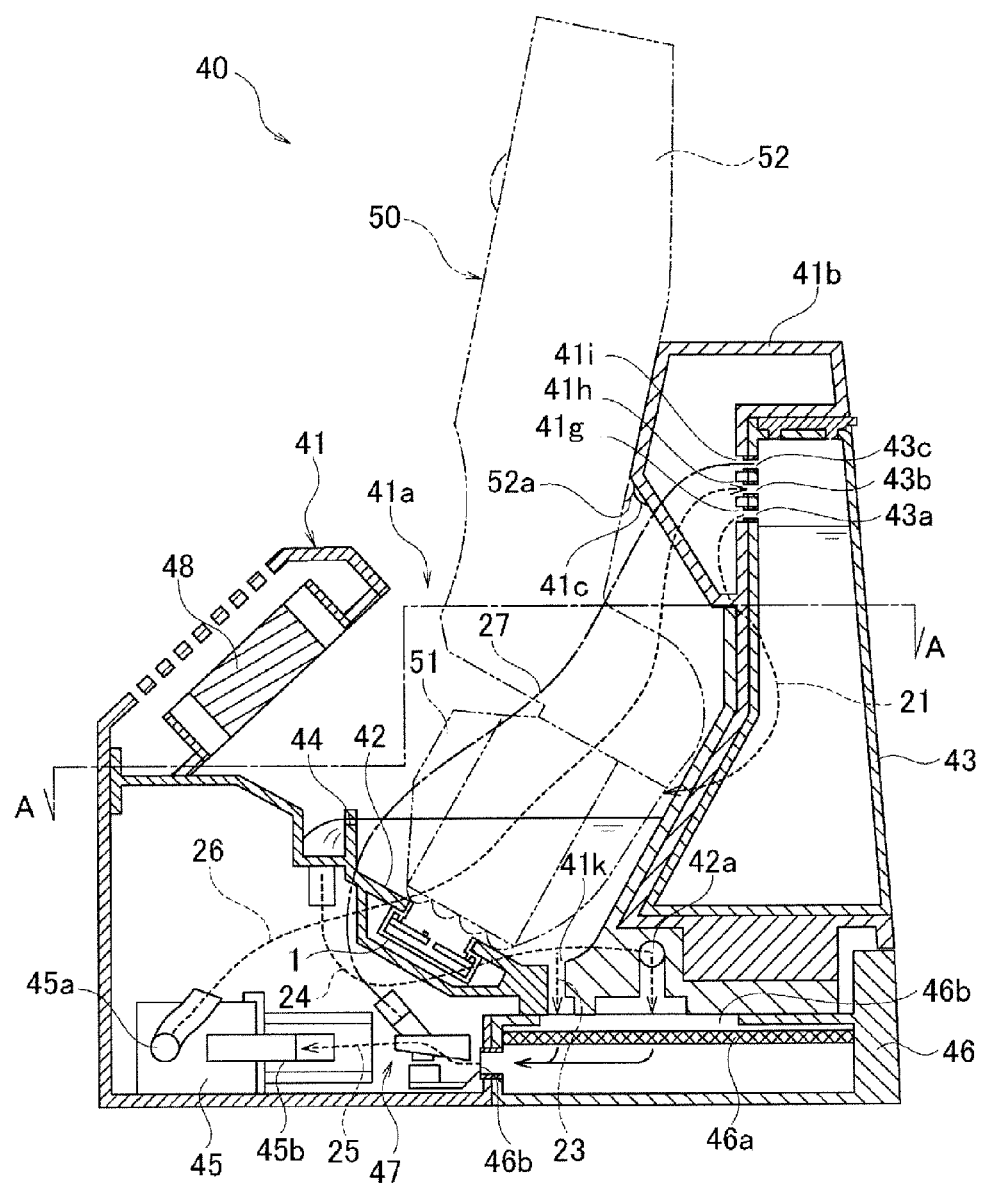
FIG. 9 is a side cross-sectional view showing a small-sized appliance according to an embodiment of the present invention.

As shown in FIG. 9, when the cleaning and purifying apparatus is used in usage mode A, the upper wall of the case member 2 in the plasma generator 1 may be open so as to soak the head unit 51 in the liquid 17 cleaned and purified in the case member 2. This also contributes to efficiently resolving the organic substances adhering to the head unit 51 as in the case of usage mode B.

As described above, in the present embodiment, since the cleaning and purifying apparatus (the small-sized appliance) 40 includes the plasma generator 1, the small-sized appliance capable of efficiently producing a large amount of radicals can be obtained.

Although the present invention has been described above by reference to the preferred embodiments, the present invention is not limited to the descriptions thereof, and it will be apparent to those skilled in the art that various modifications and improvements can be made.

Although the respective embodiments use the ceramic member as the partition provided with the gas passage, the partition is not limited to the ceramic member. For example, the partition may be obtained in such a manner that an arbitrary member such as a glass plate to separate a gas from a liquid is prepared, and it is then subjected to photoengraving and etching processing so as to provide fine pores having a diameter approximately in the range from 1 μm to 10 μm.

The partition may be provided with plural gas passages.

The cleaning and purifying apparatus and the small-sized appliance are not particularly limited to those in the respective embodiments described above. For example, the present invention is applicable to, for example, a cleaning and purifying apparatus for an electrical toothbrush, a water filtration apparatus, and an apparatus for purifying water containing detergents before discharging.

The liquid storage section, the gas storage section and the other particular specs (such as a shape, size and layout) can also be changed as necessary.

The entire content of Japanese Patent Application No. P2011-024933 (filed on Feb. 8, 2011) is herein incorporated by reference.

INDUSTRIAL APPLICABILITY

The present invention is applicable to a plasma generator required to produce a large amount of radicals efficiently, and applicable to a cleaning and purifying apparatus and a small-sized appliance using the plasma generator.

REFERENCE SIGNS LIST

1 Plasma generator
3 Ceramic member (partition)
3a Gas passage

4 Liquid storage section
5 Gas storage section
10 Pipe (gas introduction passage)
11 Gas supply unit
12 First electrode
13 Second electrode
15 Plasma power source
20 Cleaning and purifying apparatus
21 Pipe (the liquid introduction passage)
22 Pipe (the liquid discharge passage)
40 Cleaning and purifying apparatus (small-sized appliance)
60 Voltage controller
61 Sensing member

The invention claimed is:

1. A plasma generator, comprising:
a liquid storage section that stores a liquid containing water;
a gas storage section that stores a gas;
a partition provided with a gas passage to introduce the gas in the gas storage section into the liquid storage section, and separating the liquid storage section from the gas storage section;
a first electrode provided in the gas storage section;
a second electrode separated from the first electrode and provided in a manner such that at least a portion coupled with the first electrode is in contact with the liquid in the liquid storage section;
a gas supply unit that supplies a gas containing oxygen to the gas storage section so that the gas in the gas storage section is delivered under pressure into the liquid storage section via the gas passage;
a plasma power source that applies a predetermined voltage between the first electrode and the second electrode to cause electric discharge between the first electrode and the second electrode, and thereby convert the gas introduced into the gas storage section into plasma;
a voltage controller that controls the voltage applied by the plasma power source depending on a condition of the liquid in the liquid storage section, and
a sensing member that senses an impedance of the liquid in the liquid storage section at a fixed time interval,
wherein the voltage controller controls the plasma power source to apply a higher voltage between the first electrode and the second electrode as the impedance of the liquid sensed by the sensing member increases, and controls the plasma power source to apply a lower voltage between the first electrode and the second electrode as the impedance of the liquid sensed by the sensing member decreases.

2. The plasma generator according to claim 1, wherein the sensing member senses a temperature of the liquid in the liquid storage section at a fixed time interval,
wherein the voltage controller controls the plasma power source to apply a higher voltage between the first electrode and the second electrode as the temperature of the liquid sensed by the sensing member increases, and controls the plasma power source to apply a lower voltage between the first electrode and the second electrode as the temperature of the liquid sensed by the sensing member decreases.

3. The plasma generator according to claim 1, wherein the sensing member senses a pH of the liquid in the liquid storage section at a fixed time interval,
wherein the voltage controller controls the plasma power source to apply a lower voltage between the first electrode and the second electrode as the pH of the liquid sensed by the sensing member increases, and controls the plasma power source to apply a higher voltage between the first electrode and the second electrode as the pH of the liquid sensed by the sensing member decreases.

4. The plasma generator according to claim 1, wherein the sensing member senses a presence or absence of gas bubbles in the liquid in the liquid storage section at a fixed time interval,
wherein the voltage controller controls the plasma power source to apply a voltage between the first electrode and the second electrode only when the gas bubbles are sensed in the liquid in the liquid storage section.

5. A cleaning and purifying apparatus comprising the plasma generator according to claim 1.

6. A small-sized appliance comprising the plasma generator according to claim 1.

* * * * *